United States Patent [19]
Atkinson et al.

[11] Patent Number: 5,457,576
[45] Date of Patent: Oct. 10, 1995

[54] NEGATIVE ABBE NUMBER RADIAL GRADIENT INDEX RELAY, METHOD OF MAKING, AND USE OF SAME

[75] Inventors: Leland G. Atkinson, Rochester; Douglas S. Kindred, Springwater; Duncan T. Moore, Fairport; J. Robert Zinter, Rochester; J. Raymond Hensler, Rochester, all of N.Y.

[73] Assignee: Gradient Lens Corporation, Rochester, N.Y.

[21] Appl. No.: 147,402

[22] Filed: Nov. 5, 1993

Related U.S. Application Data

[63] Continuation-in-part of Ser. No. 17,034, Jan. 28, 1993, Pat. No. 5,361,166.

[51] Int. Cl.$^6$ .................................................. G01B 3/02
[52] U.S. Cl. ................................................ 359/654; 359/435
[58] Field of Search .............................. 359/654, 435

[56] References Cited

U.S. PATENT DOCUMENTS

| | | | |
|---|---|---|---|
| 3,626,194 | 12/1971 | Hirano et al. | 359/654 |
| 3,827,785 | 8/1974 | Matsushita et al. | 359/654 |
| 3,936,149 | 2/1976 | Imai | 359/654 |
| 4,515,444 | 5/1985 | Prescott et al. | 359/654 |
| 4,641,927 | 2/1987 | Prescott et al. | 359/654 |
| 4,648,221 | 8/1987 | Takada | 359/654 |
| 4,755,029 | 7/1988 | Okabe | 359/654 |
| 4,770,506 | 9/1988 | Baba. | |
| 5,032,000 | 7/1991 | Shingaki et al. | |
| 5,182,672 | 1/1993 | Mukai et al. | 359/655 |
| 5,235,464 | 8/1993 | Tsuchida. | |
| 5,361,166 | 11/1994 | Atkinson et al. | 359/654 |

FOREIGN PATENT DOCUMENTS

| | | | |
|---|---|---|---|
| 181727 | 5/1986 | European Pat. Off. | 359/654 |
| 2638999 | 3/1977 | Germany | 359/654 |
| 6354 | 1/1980 | Japan | 359/654 |
| 5220 | 1/1986 | Japan | 359/654 |
| 4181908 | 6/1992 | Japan. | |

*Primary Examiner*—John T. Kwon
*Assistant Examiner*—Assistant Examiner
*Attorney, Agent, or Firm*—Cumpston & Shaw

[57] ABSTRACT

Radial gradient index of refraction (GRIN) optical relays for overcorrecting axial chromatic aberration and a method for their manufacture are described. A relay including a radial GRIN rod in combination with a holographic optical element, or simple homogeneous or GRIN lenses, is described for adjusting axial chromatic and monochromatic aberrations, including spherical, coma, astigmatism, and distortion. The invention also describes remote viewing scopes, such as endoscopes and borescopes, which utilize said relays for achromatic, and reduced or corrected monochromatic aberration imaging. The use of segmented said relays provides a slight degree of flexibility in certain remote viewing scopes. A method for producing an exemplary negative dispersion GRIN lens is disclosed.

22 Claims, 7 Drawing Sheets

PRIOR ART

NEGATIVE ABBE NUMBER RADIAL GRADIENT INDEX RELAY, METHOD OF MAKING, AND USE OF SAME

This is a continuation-in-part application of Ser. No. 08/017,034, filed Jan. 28, 1993, now U.S. Pat. No. 5,361, 166.

BACKGROUND OF THE INVENTION

1. Field of the Invention

This invention relates generally to gradient index ("GRIN") lenses, and specifically to a method for making, and the use of positive and negative Abbe number radial GRIN rod lenses as optical relays in endoscopes, borescopes, and similar type instruments referred to hereinbelow as "remote viewing scopes".

2. Description of the Related Art

Remote viewing scopes are well known in the art for their use in viewing, through relatively small openings, body cavities and industrial vessels, for example, where direct viewing is not possible. A typical early scope instrument is described by Hopkins in U.S. Pat. No. 3,257,902. It employs a series of rod lenses forming an objective system and a relay system for forming and relaying the image of an object down a narrow tube to a camera.

Systems of this type typically undercorrect axial chromatic aberration due to the convex, or positive, refracting surfaces of the lenses which are necessary to converge light and form real images. The aberration appears as a halo around the image because the blue light components of the image are focused closer to the lens than the red components along the optical axis. Ideally, an image formed in whim light would have a common focus for all wavelengths or colors and thus be a clear and true representation of the object being viewed.

Since classical optical elements having negative power, i.e. concave refracting surfaces, characteristically overcorrect axial color by focusing the red components closer to the lens than the blue components, axial chromatic aberration in the image formed by a Hopkins-type scope is correctable by appropriately using additional negative power lenses in the device. This approach, however, adds to complexity and cost, especially in view of the frequency of use and sterilization requirements of modem devices of this type. Leiner and Prescott, in *Applied Optics* 22, 3 p. 383 (1983) also point to difficulties in manufacturing classical lenses of the required size and surface contours for use in scope-type instruments.

Around 1970, Nippon Sheet Glass (NSG) developed solid gradient index rod lenses for use in scope-type optical systems. An advantage of the NSG GRIN rods was their flat refracting surfaces. In addition, it was realized that light rays propagating through the lens follow a sinusoidal path having a defined period when the index gradient profile varies essentially parabolically as a function of lens radius. The rod lens could then be cut to a design length corresponding to the periodicity of the light propagation path to achieve desired imaging results. Axial and radial gradient index lenses are now well known in the art. Moore et al. in U.S. Pat. No. 3,729,253, describe gradient index properties and cite references to the design and manufacture of GRIN rods used, for example, as image relays. The disadvantage of GRIN lenses produced by NSG and others, however, results from their characteristically high dispersion. High dispersion, whether positive or negative, does not contribute to good image quality which is valued in applications utilizing remote viewing scopes. Surprisingly, NSG and others who have made radial gradient lenses for years have not produced a negative radial GRIN dispersion material, or even very low positive dispersion despite the knowledge that positive dispersion is a major limitation in many imaging applications, particularly remote viewing scope relays.

An inherent problem of all conventional lenses is the chromatic aberration created by dispersion of the lens material itself. Optical dispersion is the change in the index of refraction as a function of the wavelength of the light passing through the lens. In general, the refractive index of a material is larger in shorter wavelengths than in longer wavelengths. Thus, the index of refraction in blue fight is greater than in red light. Positive dispersion, therefore, is responsible for undercorrected axial color in optical systems. Similarly, dispersion of a GRIN lens also contributes to axial chromatic aberration.

Thus the inventors recognize a need for GRIN components which characteristically overcorrect axial color, and which can be used to simplify the optical systems of remote viewing scopes for color corrected imaging. A remote viewing scope utilizing this invention is particularly useful, for example, in dental applications and has several advantages over presently available dental remote viewing scopes. The gradient index relay is lower in cost than conventional relay technologies and can be made in smaller diameters, allowing more room in a patient's mouth for illumination and dental work. In addition, a short focal length objective in connection with the gradient index relay gives increased depth of focus over conventional systems. Furthermore, the negative dispersion of the gradient index relay balances the positive axial aberration inherent in optical lenses with net positive power.

It is therefore an object of this invention to use negative dispersion GRIN lenses in the optical systems of remote viewing scopes to reduce or eliminate axial chromatic aberration in the image.

It is a further object of the present invention to use negative dispersion GRIN rods in integral and/or optical combination with conventional optical components in remote viewing scopes to reduce or eliminate spherical aberration and coma in addition to axial chromatic aberration in the image.

It is another object of this invention to use radial GRIN lenses in optical and/or integral combination with diffractive or holographic optical elements in remote viewing scopes for axial chromatic aberration correction.

It is a still further object of the present invention to use a plurality of radial GRIN rod lens segments or sections in a remote viewing scope to give such a device a degree of physical flexibility in addition to corrected imaging capability.

It is another object of the invention to produce remote viewing scopes having smaller diameters, greater depth of focus and better imaging qualities at reduced cost over remote viewing scopes having similar characteristics using conventional technology.

Finally, it is an object of this invention to provide a method of producing a negative dispersion radial gradient index relay.

SUMMARY OF THE INVENTION

The present invention uses negative dispersion radial gradient index rod lenses to overcorrect axial chromatic aberration. The invention also uses negative dispersion radial GRIN rods in combination with undercorrecting axial color elements such as objectives and viewing systems, and radial GRIN rods in combination with diffractive optical elements, in remote viewing scopes, for axial color and monochromatic aberration corrected imaging.

Dispersive characteristics of conventional, or homogeneous, optical materials used for imaging in visible light are defined, in part, by the homogeneous Abbe number ($V_{homo}$) of the lens, expressed by $$V_{homo.} = (N_d - 1)/(N_F - N_C),$$

where $N_d$ is the material index of refraction for the helium d line (yellow light), and $N_F$ and $N_C$ are the indices of refraction for the hydrogen F line (blue light) and the hydrogen C line (red light), respectively. The quantity $N_F - N_C$ is a measure of the dispersion of the material, while the Abbe number defines the dispersion relative to the amount of bending that a light ray undergoes in the material at the central d wavelength.

Every transparent material exhibits a higher index of refraction in blue than in red light (i.e., $N_F > N_C$), resulting in positive dispersion and undercorrected axial color. In contrast to a homogeneous optical element, however, the glass composition of a radial GRIN lens varies spatially as a function of lens radius, so that the Abbe number, as well as the index of refraction, also vary on a point-by-point basis with lens radius. In a radial GRIN lens the bending of the light depends on the refractive index of the lens material as well as on the change in refractive index with radius. Therefore, the chromatic aberration from a radial GRIN lens depends on the refractive index profile of the lens as well as on the dispersion of the base material. In further contrast to a homogeneous lens, the change in refractive index in a GRIN material can be larger in red light than in blue light, even though the absolute refractive index at any point in the material is larger in blue than in red light. In this case the GRIN material is said to have negative dispersion. Because the refractive index change determines the amount by which the light rays will be bent, a negative dispersion GRIN lens produces overcorrected axial chromatic aberration that can be used to compensate for undercorrected axial color arising from positive elements in an optical system.

The index of refraction profile for a radial GRIN material is expressed by $$N_\lambda(r) = N_{00,\lambda} + N_{10,\lambda} r^2 + N_{20,\lambda} r^4 + \ldots,$$

where r is the radial distance from the optical axis, and $N_{ij,\lambda}$ are constants which describe the index gradient at a particular wavelength. A radial gradient Abbe number ($V_{10}$) is defined by $$V_{10} = N_{10,d}/(N_{10,F} - N_{10,C}).$$

When the coefficient $N_{10}$ has an absolute value that is greater in the blue (F line) than in the red (C line) portion of the spectrum, the value of $V_{10}$ is positive and acts like the positive Abbe number of a homogeneous lens. In the gradient index case, on the other hand, when $N_{10}$ is greater in absolute value in red light than in blue light, $V_{10}$ is negative, and the lens is said to have negative dispersion. Since homogeneous lenses cannot exhibit negative Abbe values, a principal advantage in axial color correction from negative dispersion GRIN materials is recognized.

The invention thus discloses the use of negative Abbe number GRIN relays which overcorrect axial chromatic aberration in remote viewing scopes and the use of which results in reduced or substantially corrected axial chromatic aberration in the final image. The properties of negative Abbe value GRIN lenses have been thoroughly modeled and the manufacture of glass materials having radial index gradients is known to those skilled in the art. Such design and manufacturing techniques are described, for example, by Fantone, *Design, Engineering and Manufacturing Aspects of Gradient Index Optical Components*, PhD Thesis, The Institute of Optics, University of Rochester, New York (1979); Fantone, *Refractive Index and Spectral Models for Gradient-Index Materials*, Applied Optics 22, 3 p. 432 (1983); Ryan-Howard and Moore, *Model for the Chromatic Properties of Gradient Index Glass*, Applied Optics 24, 24 p. 4356 (1985); and Kindred, *Development of New Gradient Index Glasses For Optical Imaging Systems*, PhD Thesis, The Institute of Optics, University of Rochester, New York (1990). Ryan-Howard did produce some negative dispersion gradients using ion exchange in a Schott KF3 glass and measured a GRIN V number from −148 to −255; however, KF3 glass contains no $LiO_2$ which precludes making a radial GRIN relay from that material by $Na^+$ for $Li^+$ exchange, as set forth in the instant invention. Kindred actually produced an optical component consisting of a thin slab of material having a radial gradient index and a net negative Abbe number that was capable of image formation when immersed in an index matching liquid; however, negative Abbe number radial GRIN relays, in particular, are not previously described by those skilled in the art. The invention further describes a method for making an exemplary embodiment of the negative dispersion radial gradient index relay for producing the desired negative V number and gradient partial dispersion.

The present invention describes novel uses and applications of radial gradient index rod lenses. The invention further discloses the use of negative Abbe value radial GRIN rod lenses with variable combinations of planar and non-planar refracting surfaces for monochromatic aberration adjustment as well as achromatic imaging. Non-planar refractive GRIN rod surfaces are achieved by attaching, or optically combining, homogeneous or GRIN non-plano-plano elements and the GRIN rods. GRIN rods can also be combined with holographic or diffractive optical elements to produce specific amounts of over- or undercorrected axial chromatic aberration in addition to reducing spherical aberration and coma. Furthermore, spherical aberration and coma from a GRIN lens can be reduced by adjusting the fourth and higher order expansion terms of the radial gradient index of refraction, as is well known by those skilled in the art.

The invention further discloses optical relays in remote viewing scopes comprising positive and negative Abbe number radial GRIN rods in which the rods are cut into segments for adding limited flexibility to a normally rigid orthopedic endoscope, for example. In this case, the rods are cut into lengths such that no intermediate images are formed at any lens/air interface of the relay system. Light rays follow a sinusoidal path through the GRIN rod of the invention, in which the pitch, $P_{80}$, of the lens, or equivalently, the period of the sinusoidal light path, is described by $$P_\lambda = 2\pi \sqrt{N_{00,\lambda}/-2N_{10,\lambda}}$$

As intermediate images are formed at every half-period distance, a paraxial axial ray will attain its greatest amplitude at every first and third one-quarter pitch point ($P_{80}/4$) of the lens when the image initially falls on the first face of the GRIN rod; the one-quarter pitch point being expressed by $$P_\lambda/4 = \pi/2 \sqrt{N_{00,\lambda}/-2N_{10,\lambda}}$$

The invention also describes segmented negative dispersion radial GRIN rods for use in remote viewing scope relay systems wherein baffles are located slightly to the object side of selected one-quarter pitch positions for reducing scatter from off-axis illumination vignetted by the rod lens.

BRIEF DESCRIPTION OF THE DRAWINGS

FIG. 7 is a line drawing of an optical relay having at least one negative Abbe number GRIN rod as shown in FIG. 2. FIG. 7 also shows the sinusoidal fight path that light takes as it propagates through the GRIN rod;

DETAILED DESCRIPTION OF THE INVENTION

Figure 1:
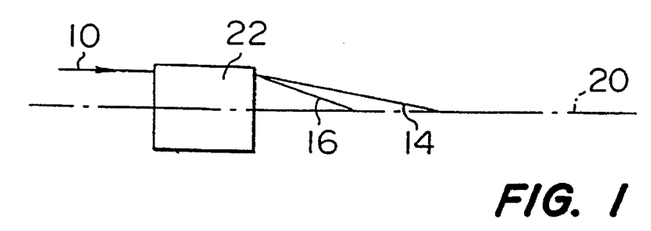
FIG. 1 is a line drawing of a negative dispersion optical element.

Having described the various objects, advantages, and applications of the present invention, reference is now made to the drawings in which FIG. 1 shows a diagrammatic illustration of a negative dispersion, negative Abbe number radial GRIN element 22 which focuses the red component 16 of the incident white light 10 nearer the lens than the blue component 14 along optical axis 20; the lens overcorrects axial chromatic aberration.

Figure 2:
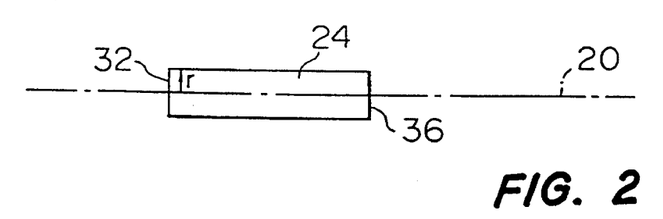
FIG. 2 shows a negative Abbe number radial GRIN rod having plane parallel end faces normal to the optical axis.

A preferred embodiment of the present invention is shown in FIG. 2 in which the negative Abbe number radial GRIN component is a rod lens 24 having an essentially parabolic variation of refractive index as a function of lens radius r, described by the expression $$N_\lambda(r) = N_{00,\lambda} + N_{10,\lambda} r^2 + N_{20,\lambda} r^4 + N_{30,\lambda} r^6 + \ldots ,$$

where $N_{00,\lambda}$ is the base refractive index of the material and $N_{ij,\lambda}$ are constants which describe the index gradient at a particular wavelength $\lambda$, where $N_{10}$ has units of mm$^{-2}$. In particular, $N_{10,\lambda}$ relates to the period $P_\lambda$ of the sinusoidal propagation of light through the lens, defined by $$P_\lambda = 2\pi \sqrt{N_{00,\lambda}/-2N_{10,\lambda}} \quad ;$$

while the higher order index terms provide adjustment for monochromatic aberrations such as spherical aberration and coma.

In addition to overcorrecting axial color with a negative Abbe number radial GRIN material exhibiting negative dispersion, monochromatic aberrations, like spherical aberration and coma, can also be reduced or eliminated by the selective combination of curvatures of the GRIN rod end faces.

Figure 3:
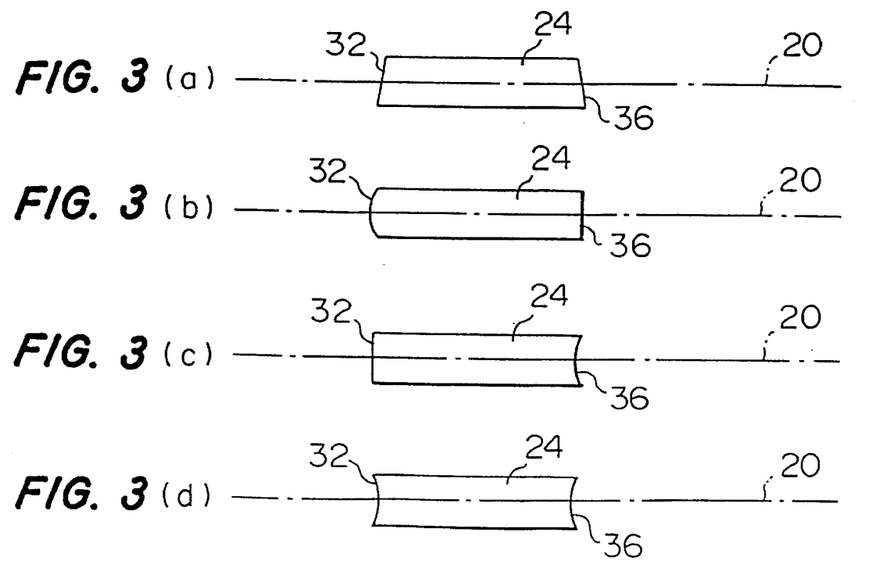
FIGS. 3(a)–(d) show the GRIN rod of FIG. 2 having various end face contours for adjusting selected monochromatic aberrations.

FIG. 3 diagrammatically illustrates four examples of GRIN rod 24 having variously contoured first and second end faces 32, 36. Specifically, FIG. 3(a) shows GRIN rod 24 with planar faces 32, 36 not normal to optical axis 20. FIG. 3(b) shows a spherical-convex first face 32 and a plano rear face 36 on GRIN rod 24. FIG. 3(c) shows GRIN rod 24 with plano front face 32 mad spherical-concave rear face 36; while FIG. 3(d) shows the GRIN rod having aspheric-concave front and rear faces 32, 36. It is to be understood that this embodiment of the invention is not limited only to the combinations shown but comprises all combinations of surface contours, including bi-convex and bi-concave.

Figure 4:
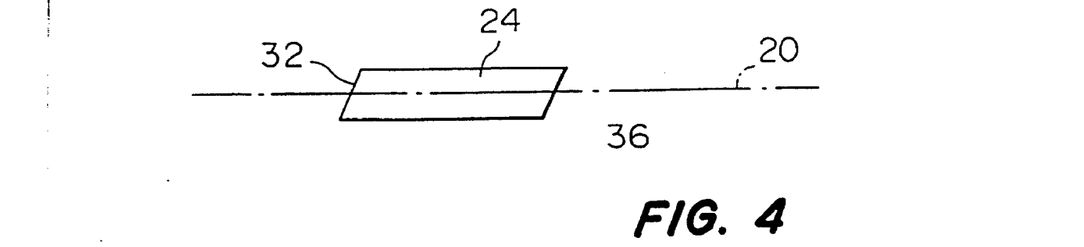
FIG. 4 is a line drawing of the rod lens of FIG. 2 in which the plane parallel end faces are not normal to the optical axis.

FIG. 4 shows another embodiment of the invention in which negative Abbe number GRIN rod 24 has plane parallel faces 32, 36 which are not normal to the optical axis 20. Further, as shown in FIG. 2, surfaces 32, 36 are plane parallel and normal to optical axis 20.

Figure 5:
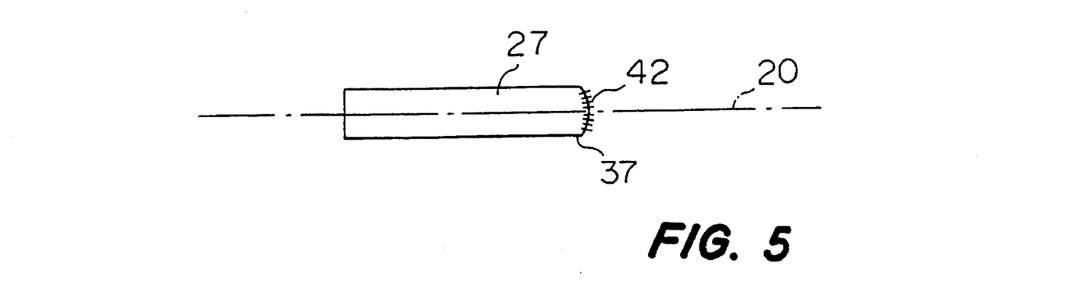
FIG. 5 is a line drawing of a positive dispersion radial GRIN rod having a holographic optic attached to one of the end faces for overcorrecting axial chromatic aberration.

It is well known in the art that diffractive, or holographic, optical elements characteristically overcorrect axial color. FIG. 5 shows an embodiment of the present invention in which a holographic optical element ("HOE") 42 is attached to the rear face 37 of radial GRIN rod 27. HOE 42 significantly overcorrects axial chromatic aberration and so is able to compensate for the undercorrected axial color characteristic of positive, or homogeneous, Abbe number optical elements typically found in remote viewing scopes. It is to be understood that the HOE need not be physically connected to the GRIN rod; equivalent overcorrection is achieved when the HOE is in direct optical contact with the GRIN rod.

Figure 6:
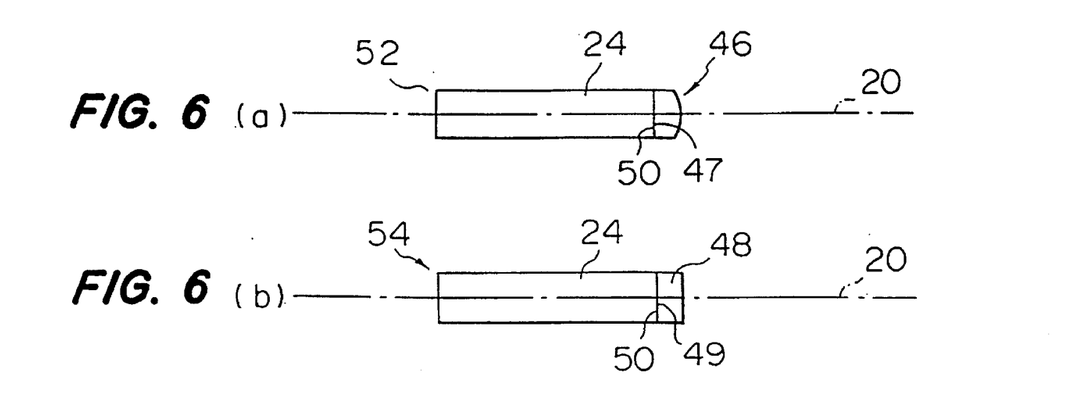
FIGS. 6(a) and 6(b) are line drawings of the negative Abbe number radial GRIN rod of FIG. 2 with separate homogeneous and GRIN elements, respectively, attached to the rod lens for axial chromatic and monochromatic aberration adjustment.

In another embodiment of the present invention, as seen in FIGS. 6(a) and 6(b), simple homogeneous lens 46 and gradient index lens 48, respectively, are combined with negative Abbe number GRIN rod 24 to form lenses 52, 54, respectively. Lens 46 and GRIN lens 48 each have at least one planar surface 47, and 49, respectively, which form the boundary of attachment to planar face 50 of GRIN rod 24. Lenses 46, 48 are used to adjust certain monochromatic aberrations such as spherical aberration and coma, for example, and when one of the lens combinations 52, 54 are used in a remote viewing scope, the final image is color corrected and has reduced spherical aberration and coma.

Figure 7:
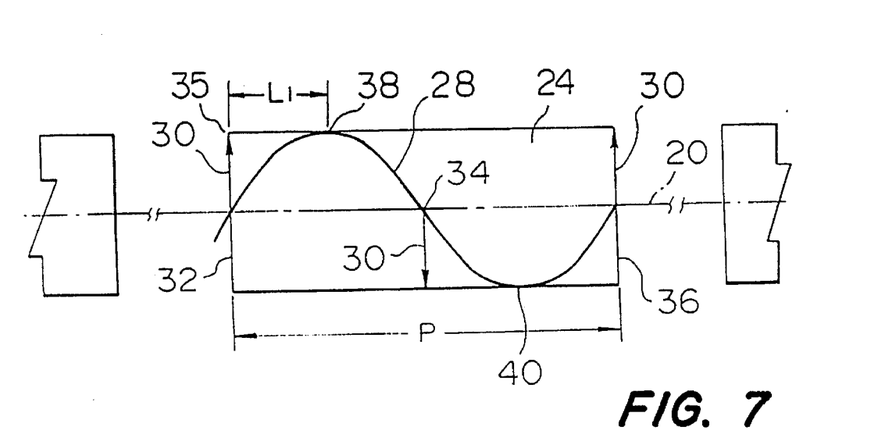

FIG. 7 shows an embodiment of the invention in which an optical relay 35 comprises at least one negative Abbe number radial GRIN rod 24. FIG. 7 particularly shows one full period $P_\lambda$ of the sinusoidal path of an on-axis axial ray 28 as it propagates through lens 24. As drawn, intermediate image 30 is formed on the front face 32 of negative Abbe number GRIN rod 24; at location 34 where axial ray 28 crosses optical axis 20; and on the rear face 36 of the lens. In this case, $L_1$ represents a one-quarter pitch length $P\lambda/4$; i.e., location 38 represents the position in lens 24 where ray 28 would exit the lens collimated if the lens was cut at that location. Likewise, location 40 shows the third one-quarter pitch position of lens 24.

Figure 8:
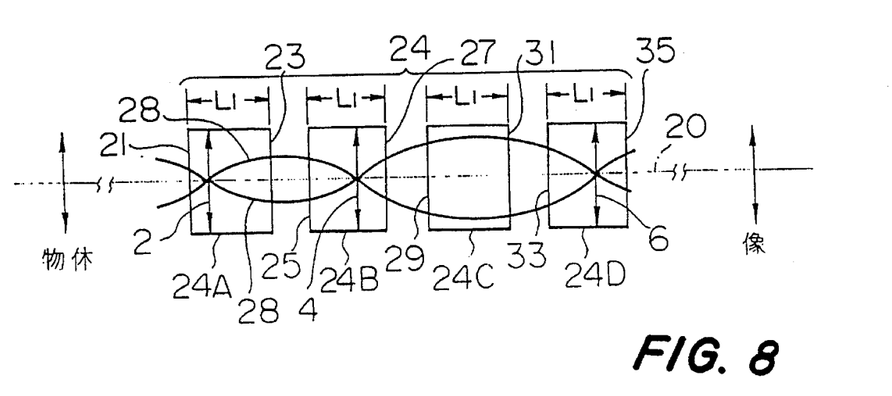
FIG. 8 is a line drawing of a negative Abbe number GRIN rod of FIG. 2 which has been cut into segments such that a remote viewing scope that incorporates the segmented relay would have limited flexibility. A ray path through the lens segments illustrates intermediate image formation.

In one embodiment of the invention, shown in FIG. 8, GRIN rod 24, comprising the relay of an orthopedic endoscope (not shown), is cut into segments 24A, 24B, 24C, and 24D to give the instrument slightly increased flexibility. Each section has a length such that intermediate images 2, 4, and 6 are formed intermediate the segment end faces 21, 23; 25, 27; 29, 31; and 33, 35 as illustrated by the intersection of the axial rays 28 with the optical axis 20.

Figure 9:
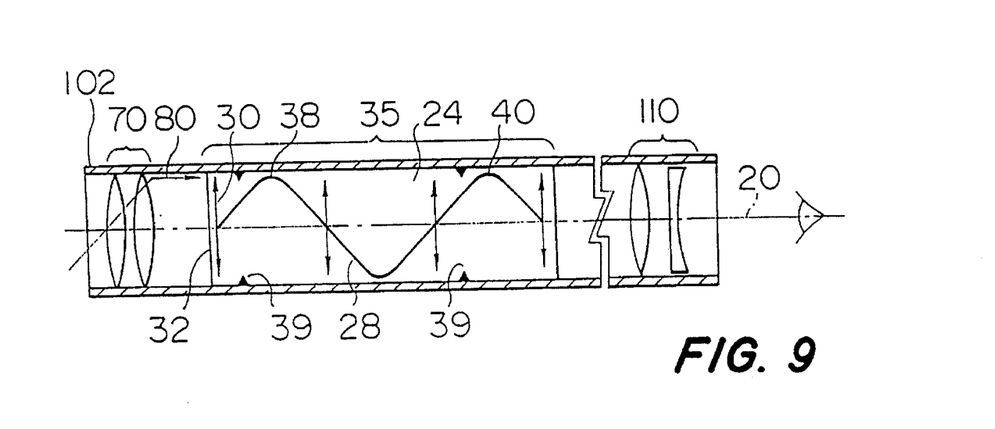
FIG. 9 diagrammatically illustrates, in cross section, a remote viewing scope including a housing and an objective system, a GRIN rod relay, and a viewing system disposed therein. For the sake of clarity, the internal lenses are not shown in cross section.

FIG. 9 shows a preferred embodiment of the invention in which an objective system 70, a relay 35, and a viewing system 110 are aligned and disposed within an endoscope housing 102. Objective group 70 is telecentric to relay system 35. In this case, marginal ray 80 from the object enters the negative Abbe number radial GRIN relay rod 24 parallel to the optical axis 20 and follows a sinusoidal path 28 through the lens as shown. The telecentric embodiment comprises at least a two element objective group 70 for increased field of view over a single objective lens. In a non-telecentric arrangement, the chief ray from the object does not enter the first GRIN relay lens parallel to the optical axis resulting in clipping of the sinusoidally transmitted light and increased scatter through the system, or the need for a relay with a larger numerical aperture. It follows from this, and with reference to FIG. 9, that when intermediate image 30 is formed on front surface 32 of GRIN rod 24, a baffle 39 located at the first and third one-quarter pitch locations 38, 40, respectively, would effectively reduce optical noise at the points of maximum axial ray height in the rod from propagating through the system. When the rays entering the relay are non-telecentric, vignetting occurs ahead or in front of the quarter-pitch locations. For this reason, baffle 39 is positioned slightly to the object side of one-quarter pitch points 38, 40, as shown in FIG. 9.

Figure 10:
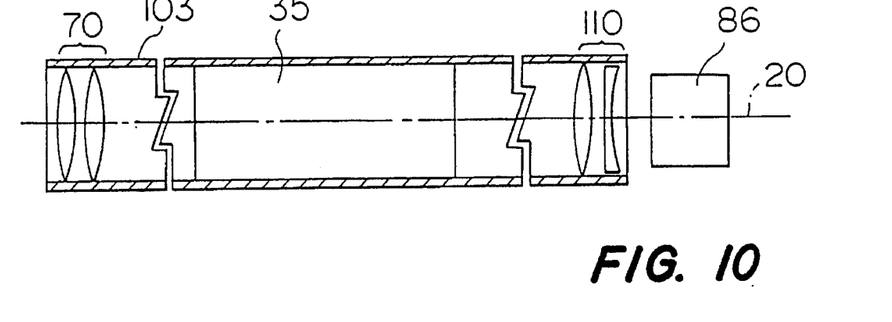
FIG. 10 shows the remote viewing scope of FIG. 9 wherein the viewer's eye is replaced by an electronic imaging sensor.

In FIG. 10, image sensing means 86, including conventional optical and electronic means, are used in combination with the viewing system 110, and in place of a viewer's eye. In this embodiment, objective system 70, relay 35, and viewing system 110 are disposed within a borescope housing 103, while image sensing means 86 remains separated from the remote viewing scope.

Figure 11:
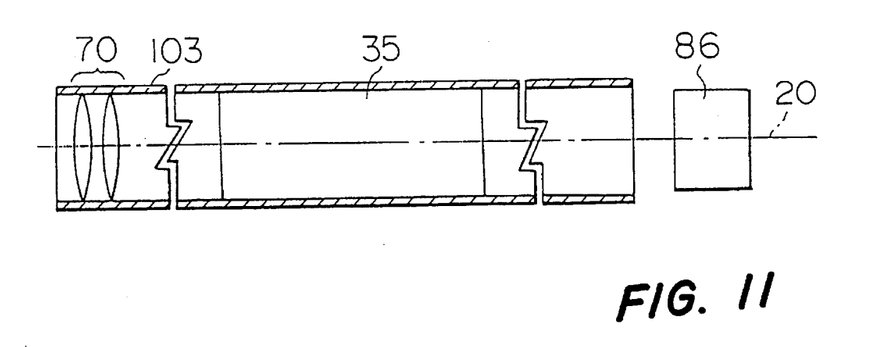
FIG. 11 shows the remote viewing scope of FIG. 10 in which an electronic imaging sensor is used without an eye piece group.

FIG. 11 shows a further embodiment of the invention in which the image sensing means 86 is used in combination with a remote viewing scope having no eyepiece 110; i.e., the image from the relay falls directly on the image sensing means 86. It is to be understood that the remote viewing scope comprising an eyepiece 110 designed for viewing the image with the eye, or by electrical or optical means alone, or the eyepiece/sensing means combination, are all embodiments of the remote viewing scope of the invention.

Figure 12:
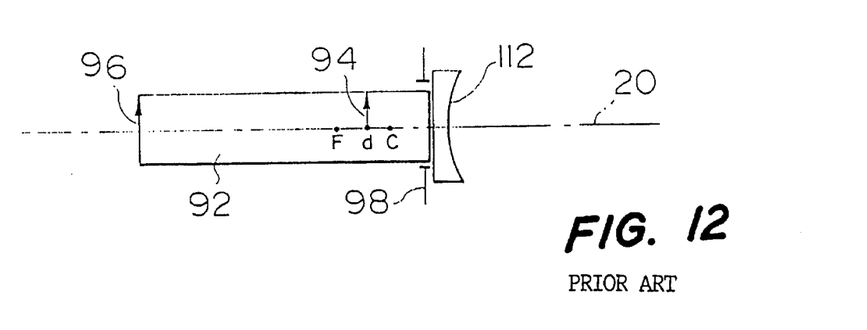
FIG. 12 is a line drawing of the prior art showing axial chromatic aberration correction by a positive Abbe number GRIN rod and a negative power homogeneous lens attached thereto.

FIG. 12 illustrates a prior art device for correcting axial chromatic aberration wherein a homogeneous plano-concave lens 112 is combined with a positive Abbe number GRIN rod 114. The axial chromatic color is corrected by forming a virtual image 94 of object 96 in front of the exit pupil 98 of the system.

Figure 13:
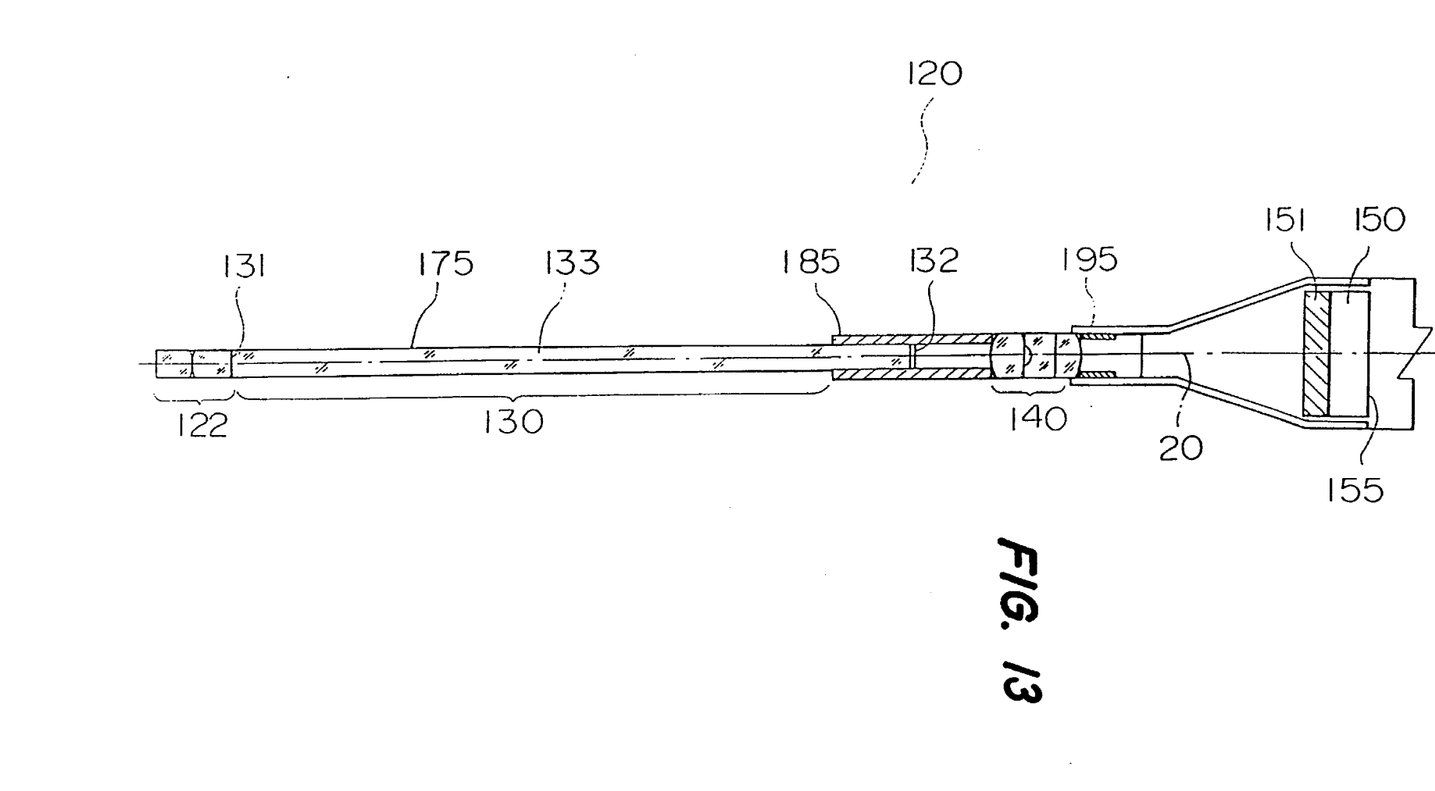
FIG. 13 is a line drawing of a preferred embodiment of the invention showing a two element objective, a negative dispersion GRIN relay, a three element coupler lens and electronic imaging means, disposed within a series of housings.
Figure 14:
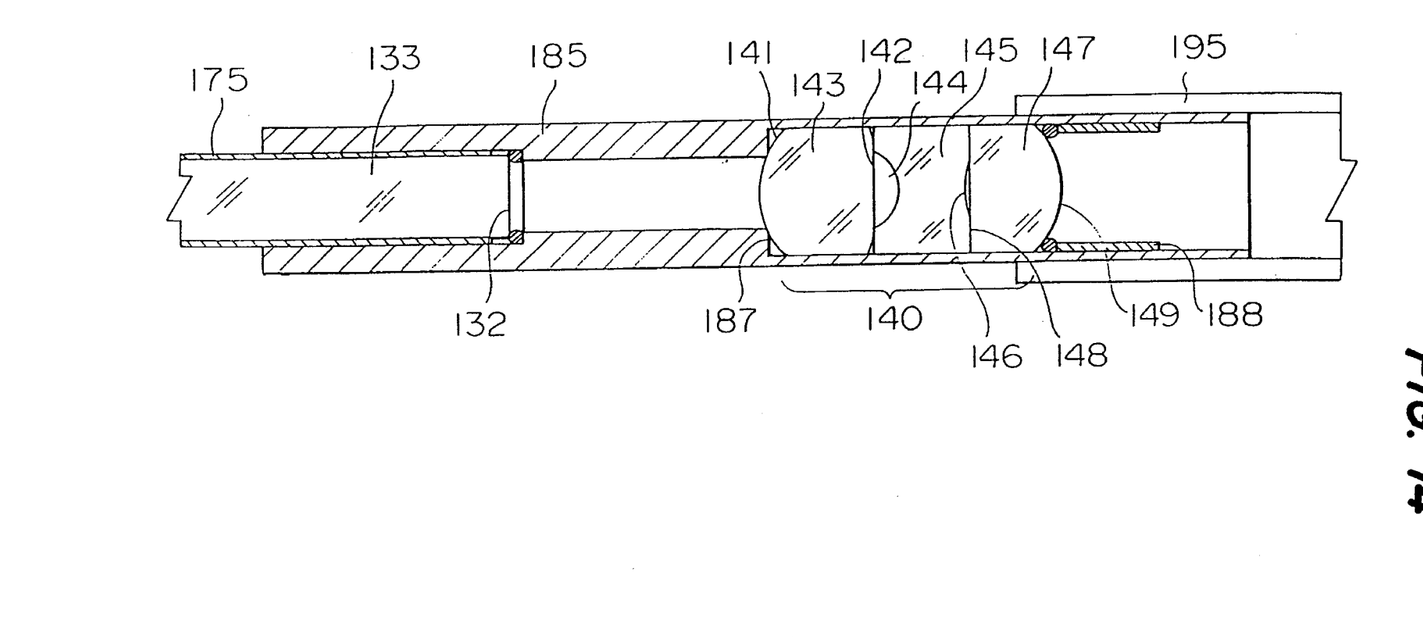
FIG. 14 is an enlarged view of the coupler lens mounted in the housing.
Figure 15:
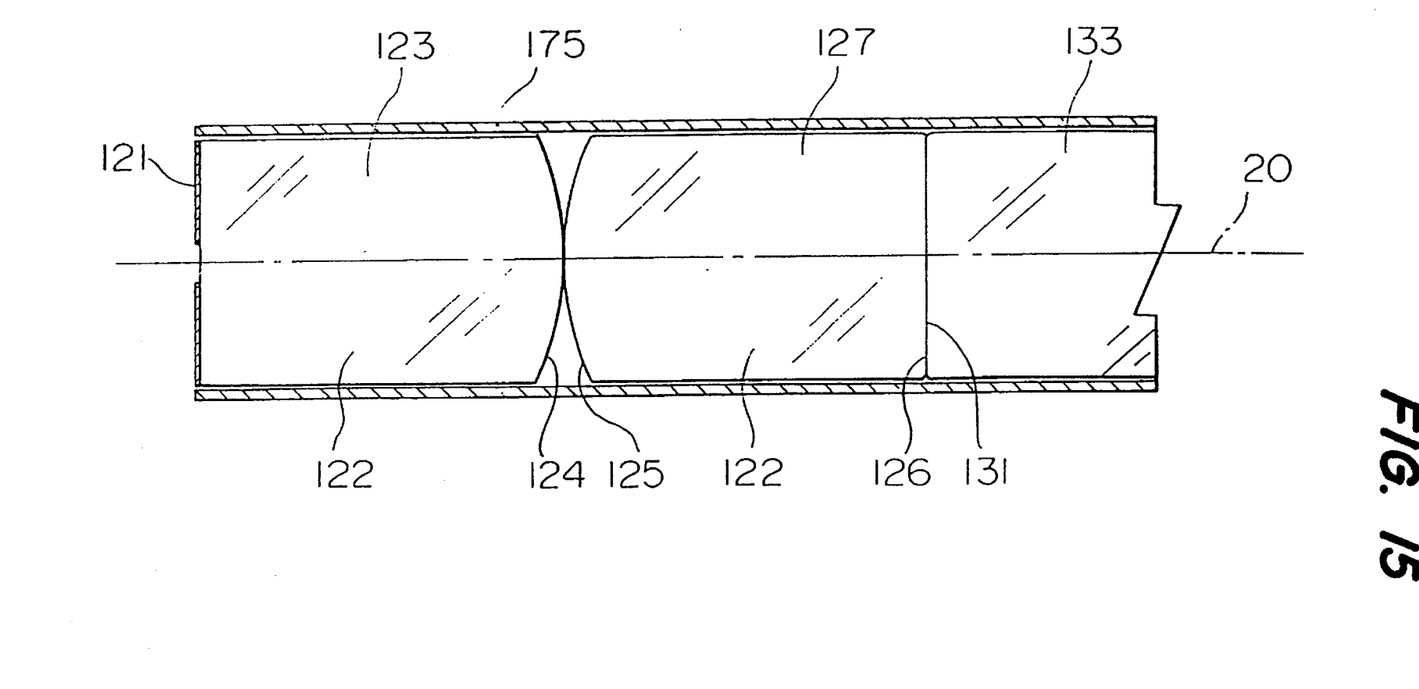
FIG. 15 shows an enlarged view of the objective as it appears mounted in the housing, including the aperture stop.

An exemplery embodiment of the invention is shown in FIGS. 13–15. A remote viewing scope 120 comprises an objective 122, a radial GRIN relay 130, a viewing system or coupler lens 140 and electronic imaging means 150. The objective includes an aperture stop 121, a first plano-convex lens 123 (denoted by $D_1$) and a second plano-convex lens 127 (denoted by $D_2$). First objective lens 123 includes a first refracting surface 122 (denoted by $d_1$) which is plano, and a second refracting surface 124 (denoted by $d_2$) having a convex radius of curvature denoted by $r_2$. Similarly, second objective lens 127 has a first refracting surface 125 (denoted by $d_3$) having a convex radius of curvature (denoted by $r_3$) and a second refracting surface 126 (denoted by $d_4$) that is plano. Aperture stop 121 is in contact with first refractive surface 122 of first objective lens 123 as shown in FIG. 15. Objective lenses 123 and 127 are not cemented together; however, the convex surfaces 124, 125, respectively, of objective lenses 123 and 127 are in contact. The thickness $t_{D1}$ of the first objective lens 123 is such that when the aperture stop 121 is in contact with lens 123, the objective is nearly telecentric; that is, the aperture stop is located near the front focal point of the objective. The thickness $t_{D2}$ of second objective lens 127 is such that the image plane, at the nominal object position, is either inside or outside of element 127 to reduce or eliminate poor image quality due to the effects of dust or imperfections on the element surfaces. Preferably, an object at infinity will be focused beyond second objective lens 127 to insure that the resulting image is formed beyond rear surface 126 at all object positions. The rear surface 126 of second objective lens 127 could be made slightly concave to reduce the possibility of scratching the face 131 of relay 130 during assembly. A concave surface at 126, however, may not be justified due to the higher production costs involved. Table 1 lists the radii of curvature, thicknesses, and indices of refraction of the objective lens elements.

TABLE 1

| Element | Radius of curvature | Thickness (mm) | Index |
|---------|---------------------|----------------|-------|
| $D_1$ | $r_1$ = infinity | $t_{D1}$ = 3.950000 | $n_c$ = 1.617272 |
|  |  |  | $n_d$ = 1.620409 |
|  |  |  | $n_F$ = 1.627560 |
|  | $r_2$ = −3.20000 |  |  |
| $D_2$ | $r_3$ = 3.20000 | $t_{D2}$ = 3.950000 | $n_c$ = 1.617272 |
|  |  |  | $n_d$ = 1.620409 |
|  |  |  | $n_F$ = 1.627560 |
|  | $r_4$ = infinity |  |  |

Radial GRIN relay 130 comprises at least one negative dispersion radial grin component 133 (denoted by $GR_1$) having a first refractive surface 131 (denoted by $g_1$), a second refractive surface 132 (denoted by $g_2$), a thickness $t_{R1}$ and a negative Abbe value or gradient V number in the range between negative infinity and about −50. Exemplary GRIN relay 130 has an actual Abbe value of about −175, and a gradient partial dispersion of about 0.3. A more preferable range for the gradient V number is between about −500 to −175, with an actual value of about −350 being most preferable. In this embodiment the refractive surfaces of the radial GRIN component 133 are plano, coperpendicular, and normal to the optical axis 20. First surface 131 of GRIN component 133 is in noncemented contact with surface 126 of second objective lens 127. The thickness $t_{R1}$ and gradient index coefficients $N_{00,\lambda}$, and $N_{10,\lambda}$ according to the expression for the gradient index profile $$N_{80}(r)=N_{00,\lambda}+N_{10,\lambda}r^2+\ldots,$$

of exemplary GRIN relay 130 are presented in Table 2.

TABLE 2

| Element | Thickness (mm) | $N_{00,\lambda}$ | $N_{10,\lambda}$ |
|---|---|---|---|
| $GR_1$ | $tR_1$ = 68.0000 | $N_{00c}$ = 1.531100 $N_{00d}$ = 1.534200 $N_{00F}$ = 1.540900 | $N_{10c}$ = −0.1600E-02 $N_{10d}$ = −0.1597E-02 $N_{10F}$ = −0.1591E-02 |

It will be understood by a person skilled in the art that GRIN relay 130 may comprise a plurality of GRIN rods, depending upon the ability to manufacture rods of the desired overall length and requisite optical parameters.

Approximately one-half pitch length of the gradient relay is used to relay the image formed by the objective to a second internal image plane near the second surface 132 of the gradient relay. In the exemplary design the image is located approximately 1.0 mm past surface 132 so as to minimize optical noise throughput by the system due to dust or scratches on an optical surface being focused with the image.

The exemplary embodiment of the invention further includes coupler lens 140 as shown in FIG. 14. The coupler lens includes a first refractive element 143 (denoted by $C_1$) having thickness $t_{C1}$, a convex first refracting surface 141 (denoted by $c_1$) and a convex second refracting surface 142 (denoted by $c_2$), and is a crown glass; a second refractive element 145 (denoted by $C_2$) having thickness $t_{C2}$, a concave first refractive surface 144 (denoted by $c_3$) and a concave second refractive surface 146 (denoted by $c_4$), and is a flint glass; and a third refractive element 147 (denoted by $C_3$) having thickness $t_{C3}$, a plano first refracting surface 148 (denoted by $c_5$) and a convex second refracting surface 149 (denoted by $c_6$), and is a crown glass. The respective thicknesses $t_{C1}$, $t_{C2}$, and $t_{C3}$ are adjusted such that surfaces 142 and 144 are in partial noncemented contact and surfaces 146 and 148 are likewise in partial noncemented contact. Table 3 lists the specific radii of curvature, thicknesses, and indices of refraction for the elements of the coupler lens.

TABLE 3

| Element | Radius of curvature | Thickness (mm) | Index |
|---|---|---|---|
| $C_1$ | $r_{c1}$ = 2.85000 | $t_{C1}$ = 3.575000 | $n_c$ = 1.739044 $n_d$ = 1.743998 $n_F$ = 1.755689 |
| $C_2$ | $r_{c2}$ = −9.60000 $r_{c3}$ = −1.30585 | $t_{C2}$ = 1.992000 | $n_c$ = 1.682502 $n_d$ = 1.688927 $n_F$ = 1.704609 |
| $C_3$ | $r_{c4}$ = 3.89000 $r_{c5}$ = infinity $r_{c6}$ = −2.85000 | $t_{C3}$ = 2.847000 | $n_c$ = 1.739044 $n_d$ = 1.743998 $n_F$ = 1.755689 |

Although an exemplary design of the coupler lens is provided, it will be appreciated by those skilled in the art that other designs, for example, a radial GRIN lens having overcorrected axial color, a Petzval lens configuration or a two doublet configuration, could also be used.

In the exemplary embodiment, the electronic imaging means 150 comprises a Panasonic KS 152CCD camera or other one-half inch format CCD. As shown in FIG. 13, electronic imager 150 comprises an IR rejection filter 151 and CCD 155. The optical layout of the preferred embodiment of the invention as shown FIG. 13 appears in tabular form in Table 4.

TABLE 4

| element (surface) | Radius of curv. | Thickness (mm) |
|---|---|---|
| object | | |
| aperture stop (121) | infinity | 0.20000 |
| $D_1$ (122) | infinity | |
| $D_1$ (124) | −3.2000 | 3.95000 |
| $D_2$ (125) | 3.2000 | |
| | | 3.95000 |
| $D_2$ (126) | infinity | |
| $GR_1$ (131) | infinity | |
| | | 68.0000 |
| $GR_1$ (132) | infinity | |
| paraxial image 1 | | .442116 from (131) |
| paraxial image 2 | | .999652 from (132) |
| air space | | 6.62035 to (from parax image to 141) |
| $C_1$ (141) | 2.8500 | |
| | | 3.575000 |
| $C_1$ (142) | −9.6000 | |
| $C_2$ (144) | −1.30585 | |
| | | 1.992000 |
| $C_2$ (146) | 3.89000 | |
| $C_3$ (148) | infinity | |
| | | 2.847000 |
| $C_3$ (149) | −2.85000 | |
| airspace | | 25.77971 to (151) |
| CCD (155) | | 5.1300 from (151) |
| Image | | 146.6137 from (121) |

FIGS. 13–15 also show the mechanical aspects of the exemplary embodiment of the remote viewing scope. Objective 122 and GRIN relay 130 are disposed within stainless steel housing 175. Coupler lens 140 is retained in a second housing or coupler mount 185. Housing 175 fits telescopically within housing 185 where it seats against a machined step and O-ring assembly within housing 185. A second step 187 locates the coupler lens in housing 185 at first lens surface 141, while O-ring and spacer ring assembly 188 secure the coupler lens therein. A third housing 195 contains the electronic imaging means 150 and associated electronics, housing 195 telescopically engaging housing 185 as shown.

Gradient index lenses are typically fabricated by creating a concentration profile of ions in the base glass to produce a gradient index. For example, glass containing single valence ions such as $Na^+$, $Li^+$, $K^+$, $Cs^+$, $Tl^+$, or $Ag^+$ is submerged in molten salt containing a different species of a single valence ion at an appropriate temperature and for an appropriate time period. The ions in the glass exchange with those in the salt forming a concentration gradient and thus a refractive index gradient in the glass.

A typical alkali silicate host glass comprises $Na_2O$, $Li_2O$ and $SiO_2$. A method for creating a GRIN lens having a radial gradient Abbe value ($V_{10}$) between negative infinity and about −50, and between about +100 to infinity, and preferably between about −400 to −150, in accordance with this invention comprises modifying the composition of the base glass by adding optically dispersive metal oxides, either singly or in combination, to the host glass in an amount between about 1 to 15 mole %, resulting in a host glass of the form $(X)Na_2O+(Y)Li_2O+(Z)R_mO_n+(100-X-Y-Z)SiO_2$, where X, Y and Z represent mole % amounts. The presence of the metal oxide in the base glass in these amounts has yeilded a $V_{10}$ value equal to about −175, and has the potential to yeild $V_{10}$ values approaching −400, which are preferable, while permitting the development of GRIN lenses having extremely low chromatic aberration. The oxide components comtemplated by the inventors comprise $TiO_2$, $ZrO_2$, $HfO_2$, $GeO_2$, $Al_2O_3$, $Ga_2O_3$, $Y_2O_3$, $La_2O_3$, $Ta_2O_5$, $Nb_2O_5$, $W_2O_6$, $PbO$, $BaO$, $CaO$, $ZnO$, $SrO$, $MgO$ and oxides of other metals which increase the dispersion of the host glass to values in the range between about 0.009 to 0.012, and preferably equal to about 0.0106, resulting in the gradient Abbe number in the ranges between about −50 to negative infinity and +100 to infinity. $V_{10}$ values equal to about −175 have been achieved by modifying the base glass with $TiO_2$, $Al_2O_3$ and $ZrO_2$, either alone or in combination, in amounts ranging from about 0% to 5% $TiO_2$, about 0% to 10% $Al_2O_3$ and about 0% to 10% $ZrO_2$.

In a presently preferred embodiment of this invention an alkali alumina silicate base glass was composed of 10 $Li_2O+20$ $Na_2O+5$ $Al_3O_2+4$ $ZrO_2$ +61 $SiO_2$ (mole %). The glass was drawn into rods 2.7 mm in diameter by 75 mm. long. Sodium for lithium ion exchange was performed in the rods by lowering them into a bath of molten $NaNO_3$ at 455 C. degrees for 120 hours. This method resulted in a lens having a nearly parabolic refractive index profile, a radial gradient V number ($V_{10}$) equal to about −175, and a gradient partial dispersion of about 0.3.

Although specific embodiments of the invention have been disclosed, it will be understood that the invention is not limited to the details of the foregoing constructions, which are merely exemplary, and which more clearly appear in the following appended claims.

What is claimed is:

1. A remote viewing scope, comprising:
   a plurality of conventional optical components having net undercorrected axial chromatic aberration; and
   a relay optically coupled to the plurality of conventional optical components for transmitting the image of an object to a detector, comprising at least one radial GRIN component having a negative Abbe number, in which the relay has net overcorrected axial chromatic aberration,
   whereby the image at the detector is substantially corrected for axial chromatic aberration.

2. The remote viewing scope of claim 1 in which the at least one radial GRIN component comprises a rod lens having an axial dimension greater than the its diameter.

3. The remote viewing scope of claim 1 in which the at least one radial GRIN component has an Abbe value in the range between negative infinity and about −50.

4. The remote viewing scope of claim 1 in which the at least one radial GRIN component has an Abbe value in the range preferably between about −500 and −175.

5. The remote viewing scope of claim 4 in which the plurality of conventional optical components comprise an objective, in which the objective is telecentric to the relay.

6. The remote viewing scope of claim 4 in which the plurality of conventional optical components further comprise a coupler lens.

7. The remote viewing scope of claim 6 in which the coupler lens comprises a Petzval lens configuration.

8. The remote viewing scope of claim 6 in which the coupler lens comprises a two doublet configuration.

9. The remote viewing scope of claim 6 in which the coupler lens comprises a radial GRIN lens having undercorrected axial color.

10. The remote viewing scope of claim 6 further comprising electronic imaging means optically coupled to the coupler lens.

11. The remote viewing scope of claim 10 in which the objective comprises a first refractive element $D_1$ having a first refracting surface $d_1$ and a second refracting surface $d_2$, an aperture stop substantially in contact with surface $d_1$, and a second refractive element $D_2$ having a first refracting surface $d_3$ immediately adjacent surface $d_2$ and a second refracting surface $d_4$, the refracting surfaces each having a radius of curvature $r_1$, $r_2$, $r_3$ and $r_4$, respectively; each element having a thickness $tD_1$, $tD_2$, respectively; and each element having refractive indices $n_c$, $n_d$ and $n_F$, as follows:

| Element | Radius of curvature (mm) | Thickness (mm) | Index |
|---|---|---|---|
| $D_1$ | $r_1$ = infinity | $tD_1$ = 3.950000 | $n_c$ = 1.617272 |
|  |  |  | $n_d$ = 1.620409 |
|  |  |  | $n_F$ = 1.627560 |
|  | $r_2$ = −3.20000 |  |  |
| $D_2$ | $r_3$ = 3.20000 | $tD_2$ = 3.950000 | $n_c$ = 1.617272 |
|  |  |  | $n_d$ = 1.620409 |
|  |  |  | $n_F$ = 1.627560 |
|  | $r_4$ = infinity |  |  |

12. The remote viewing scope of claim 10 in which the coupler lens comprises a first refractive element $C_1$ having a first refracting surface $c_1$ and a second refracting surface $c_2$, a second refractive element $C_2$ having a first refracting surface $c_3$ immediately adjacent surface $c_2$ and a second refracting surface $c_4$, and a hird refractive element $C_3$ having a first refracting surface $c_5$ immediately adjacent surface $c_4$ and a second refracting surface $c_6$, the refracting surfaces each having a radius of curvature $rc_1$, $rc_2$, $rc_3$, $rc_4$, $rc_5$ and $rc_6$, respectively; each element having a thickness $tC_1$, $tC_2$ and $tC_3$, respectively; $C_1$ and $C_3$ each having refractive indices $n_c$, $n_d$ and $n_F$, and $C_2$ having refractive indices $n_c$, $n_d$ and $n_F$, as follows:

| Element | Radius of curvature | Thickness (mm) | Index |
|---|---|---|---|
| $C_1$ | $rc_1$ = 2.85000 | $tC_1$ = 3.575000 | $n_c$ = 1.739044 |
|  |  |  | $n_d$ = 1.743998 |
|  |  |  | $n_F$ = 1.755689 |
|  | $rc_2$ = −9.60000 |  |  |
| $C_2$ | $rc_3$ = −1.30585 | $tC_2$ = 1.992000 | $n_c$ = 1.682502 |
|  |  |  | $n_d$ = 1.688927 |
|  |  |  | $n_F$ = 1.704609 |
|  | $rc_4$ = 3.89000 |  |  |
| $C_3$ | $rc_5$ = infinity | $tC_3$ = 2.847000 | $n_c$ = 1.739044 |
|  |  |  | $n_d$ = 1.743998 |
|  |  |  | $n_F$ = 1.755689 |
|  | $rc_6$ = −2.85000. |  |  |

13. The remote viewing scope of claim 10 in which the relay comprises at least one GRIN component $GR_1$ having a first refractive surface $g_1$ immediately adjacent surface $d_4$, a second refractive surface $g_2$ and a thickness $tR_1$, the refractive surfaces all having radii of curvature equal to infinity; the GRIN component having a V number equal to about −175.

14. The remote viewing scope of claim 13 in which the relay has gradient index coefficients $N_{00c}$, $N_{00d}$, $N_{00F}$ and $N_{10c}$, $N_{10d}$ and $N_{10F}$ in the gradient index profile expression $$N_\lambda(r) = N_{00,\lambda} + N_{10,\lambda} r^2 + \ldots ,$$

as follows:

| | |
|---|---|
| $N_{00c} = 1.531100$ | $N_{10c} = -0.1600\text{E-}02$ |
| $N_{00d} = 1.534200$ | $N_{10d} = -0.1597\text{E-}02$ |
| $N_{00F} = 1.540900$ | $N_{10F} = -0.1591\text{E-}02.$ |

15. A remote viewing scope, comprising:

an objective including an aperture stop, a first refractive element $D_1$ having a first refracting surface $d_1$ in contact with the aperture stop and a second refracting surface $d_2$, and a second refractive element $D_2$ having a first refracting surface $d_3$ at least partially in contact with $d_2$ and a second refracting surface $d_4$, the refracting surfaces each having a radius of curvature $r_1$, $r_2$, $r_3$ and $r_4$, respectively; each element having a thickness $tD_1$, $tD_2$, respectively; and each element having refractive indices $n_c$, $n_d$ and $n_F$ as follows:

| Element | Radius of curvature (mm) | Thickness (mm) | Index |
|---|---|---|---|
| $D_1$ | $r_1 = \text{infinity}$ | $tD_1 = 3.950000$ | $n_c = 1.617272$ |
| | | | $n_d = 1.620409$ |
| | | | $n_F = 1.627560$ |
| | $r_2 = -3.20000$ | $0.000000$ | |
| $D_2$ | $r_3 = 3.20000$ | $tD_2 = 3.950000$ | $n_c = 1.617272$ |
| | | | $n_d = 1.620409$ |
| | | | $n_F = 1.627560$ |
| | $r_4 = \text{infinity}$; | | | a relay optically coupled to the objective including at least one radial GRIN component $GR_1$ having a first refractive surface $g_1$ in contact with $d_4$, a second refractive surface $g_2$, a thickness $tR_1$ and a negative Abbe number, the refractive surfaces of the relay all having radii of curvature equal to infinity; the at least one GRIN component having gradient V number equal to about $-175$;

a coupler lens optically coupled to the relay, in which the coupler lens comprises a first refractive element $C_1$ having a first refracting surface $c_1$ and a second refracting surface $c_2$, a second refractive element $C_2$ having a first refracting surface $c_3$ at least partially in contact with $c_2$ and a second refracting surface $c_4$, and a third refractive element $C_3$ having a first refracting surface $c_5$ at least partially in contact with $c_4$ and a second refracting surface $c_6$, the refracting surfaces having a radii of curvature $rc_1$, $rc_2$, $rc_3$, $rc_4$, $rc_5$ and $rc_6$, respectively; each element having a thickness $t_{C1}$, $t_{C2}$ and $t_{C3}$, respectively; $C_1$ and $C_3$ each having refractive indices $n_c$, $n_d$ and $n_F$, and $C_2$ having refractive indices $n_c$, $n_d$ and $n_F$, as follows:

| Element | Radius of curvature (mm) | Thickness (mm) | Index |
|---|---|---|---|
| $C_1$ | $rc_1 = 2.85000$ | $t_{C1} = 3.575000$ | $n_c = 1.739044$ |
| | | | $n_d = 1.743998$ |
| | | | $n_F = 1.755689$ |
| | $rc_2 = -9.60000$ | | |

-continued

| Element | Radius of curvature (mm) | Thickness (mm) | Index |
|---|---|---|---|
| $C_2$ | $rc_3 = -1.30585$ | $t_{C2} = 1.992000$ | $n_c = 1.682502$ |
| | | | $n_d = 1.688927$ |
| | | | $n_F = 1.704609$ |
| | $rc_4 = 3.89000$ | | |
| $C_3$ | $rc_5 = \text{infinity}$ | $t_{C3} = 2.847000$ | $n_c = 1.739044$ |
| | | | $n_d = 1.743998$ |
| | | | $n_F = 1.755689$ |
| | $rc_6 = -2.85000$; and | | | electronic imaging means optically coupled to the coupler lens comprising a filter and a CCD including an image plane.

16. The remote viewing scope of claim 15 in which the relay has gradient index coefficients $N_{00c}$, $N_{00d}$, $N_{00F}$ and $N_{10c}$, $N_{10d}$ and $N_{10F}$ in the gradient index profile expression $$N_\lambda(r) = N_{00,\lambda} + N_{10,\lambda} r^2 + \ldots,$$

as follows:

| | |
|---|---|
| $N_{00c} = 1.531100$ | $N_{10c} = -0.1600\text{E-}02$ |
| $N_{00d} = 1.534200$ | $N_{10d} = -0.1597\text{E-}02$ |
| $N_{00F} = 1.540900$ | $N_{10F} = -0.1591\text{E-}02.$ |

17. An objective for use in a remote viewing scope including a negative dispersion radial GRIN relay having overcorrected axial chromatic aberration and a viewing system having one of corrected and undercorrected axial chromatic aberration, in which the objective comprises a first plano-convex lens and a second plano-convex lens, in which at least part of the convex surfaces of the first and second lenses are adjacent, and the axial chromatic aberration of the objective is sufficiently undercorrected to substantially eliminate axial chromatic aberration in an image of an object produced by the remote viewing scope.

18. A coupler lens for use in a remote viewing scope including a negative dispersion radial GRIN relay having overcorrected axial chromatic aberration and an objective having one of corrected and undercorrected axial chromatic aberration, in which the coupler lens is sufficiently undercorrected for axial color to substantially eliminate axial chromatic aberration in an image of an object produced by the remote viewing scope.

19. The coupler lens of claim 18 comprising a Petzval lens configuration.

20. The coupler lens of claim 18 comprising a biconvex crown element, a biconcave flint element and a plano-convex crown element.

21. The coupler lens of claim 18 comprising a two doublet configuration.

22. The coupler lens of claim 18 comprising a radial GRIN lens having undercorrected axial color.

\* \* \* \* \*